(12) United States Patent
Laerum et al.

(10) Patent No.: US 6,803,727 B2
(45) Date of Patent: Oct. 12, 2004

(54) LIGHT SYSTEM FOR USE ESPECIALLY BY OPERATING THEATRE

(75) Inventors: Frode Laerum, Oslo (NO); Erik Fosse, Oslo (NO); Ole Jacob Elle, Oslo (NO)

(73) Assignee: Medinnova SF (NO)

( * ) Notice: Subject to any disclaimer, the term of this patent is extended or adjusted under 35 U.S.C. 154(b) by 0 days.

(21) Appl. No.: 10/221,362

(22) PCT Filed: Mar. 7, 2001

(86) PCT No.: PCT/NO01/00097
§ 371 (c)(1),
(2), (4) Date: Feb. 4, 2003

(87) PCT Pub. No.: WO01/69130
PCT Pub. Date: Sep. 20, 2001

(65) Prior Publication Data
US 2003/0146719 A1 Aug. 7, 2003

(30) Foreign Application Priority Data
Mar. 14, 2000 (NO) .......................................... 2001329

(51) Int. Cl.⁷ .............................. H01J 1/60; F21V 13/00
(52) U.S. Cl. ........................ 315/129; 315/133; 362/33
(58) Field of Search ................................ 315/131, 132, 315/133, 129, 291; 362/287, 33, 296; 250/203.1; H01J 1/60; F21V 13/00

(56) References Cited

U.S. PATENT DOCUMENTS

| | | | |
|---|---|---|---|
| 3,225,184 A | | 12/1965 | Reiber |
| 3,772,506 A | | 11/1973 | Junginger |
| 3,967,107 A | * | 6/1976 | Junginger et al. ............ 362/33 |
| 4,517,632 A | * | 5/1985 | Roos .......................... 362/389 |
| 4,578,575 A | | 3/1986 | Ross |
| 4,639,838 A | | 1/1987 | Kato et al. |
| 4,712,167 A | | 12/1987 | Gordin et al. |
| 5,209,560 A | | 5/1993 | Taylor et al. |
| 5,539,626 A | * | 7/1996 | Scholz ........................ 362/249 |
| 6,431,515 B1 | * | 8/2002 | Gampe et al. ............... 248/324 |
| 6,471,363 B1 | * | 10/2002 | Howell et al. ................ 362/11 |

FOREIGN PATENT DOCUMENTS

| | | |
|---|---|---|
| DE | 1076057 B | 2/1960 |
| DE | 32 43 710 | 5/1984 |

* cited by examiner

Primary Examiner—Tan Ho
Assistant Examiner—Trinh Vo Dinh
(74) Attorney, Agent, or Firm—Nixon & Vanderhye PC

(57) ABSTRACT

A lighting system, preferably for use in operating theatres, in which at least one light source is mounted to be movable an adjustable in a single ceiling and/or wall element in the form of a prefabricated module element (4). The light sources in each module element may be controlled singly or in clusters by means of a control device designed to direct the source or sources to focus at a point defined by an optical, ultrasound or magnetic, radio frequency pointer that is seen by an appropriate sensor/camera system or receiver in the room, and which, via control means, moves the light source to the desired position. The light source consists of light-emitting diodes, halogen bulbs or the end of one or several fiber-optical cables, fixed ion a holder shaped as one half of a cup or a sphere, the holder being arranges to be movable about two perpendicular axes in the xy-plane (the ceiling plane) of the ceiling module (4). The holder is attached to the ceiling element by means of a gyroscopic suspension system or a ball joint suspension system. On the top of the holder, which is at the back of the ceiling module (4), there is provided two attachment points (16, 17) offset by 90° with respect to each other but parallel to the plane of the ceiling when the light beam is directed downwards normal to the ceiling plane (xy-plane), respective linear actuators being articulated to the attachment points for reciprocating movement, so as to rotate the holder about the x-axis and the y-axis, respectively. This can also be done by use of rotary actuators, possibly mounted in combination with a gear unit, which rotate the suspension ball/holder directly about the axis of rotation.

15 Claims, 2 Drawing Sheets

LIGHT SYSTEM FOR USE ESPECIALLY BY OPERATING THEATRE

This application is the US national phase of international application PCT/NO01/00097 filed Mar. 7, 2001, which designated the US The present invention regards a lighting system for operating theatres and similar, as stated in the preamble of Claim 1.

Up until now, it has been common practice to use operating lamps that are suspended from the ceiling or are designed as projecting wall fittings or a form of standard lamp, and which, through manual or remote control, can be directed at a desired working area. A disadvantage of these known lamp systems is that they constitute a hindrance to the work of the operating personnel. A further disadvantage of existing lamps in premises (operating theatres) with ventilation discharge and extraction from the ceiling, is that these lamps have an upper side where turbulence and raising of particles will occur, thus creating favourable conditions for bacteria, which naturally is undesirable in an operating theatre, where the aim is total sterility.

The aim of the present invention is to avoid the disadvantages of previously known lighting systems.

Further, the invention aims to provide a lighting system that automatically focuses the light on the site of the operation without manual operation of the light sources, and which may readily be adjusted with regard to light intensity.

It is previously known to remotely control light sources from a control panel via a computer system, cf. U.S. Pat. No. 5,209,560, which shows a stage lighting system. Each lamp/lighting unit has a built-in microprocessor that is connected to the control panel via the computer system, the intensity of the light and the degree of light scatter being controlled from the control panel. This is a rather complex system especially designed for use within the theatre, and it is rather unsuitable for and difficult to convert to use in an operating theatre.

U.S. Pat. No. 4,712,167 describes mechanised movements of lighting units, which movements may be controlled a remote control, and which unit is especially intended for outdoor use.

As mentioned, these known systems are not very suitable for use in an operating theatre, and the aim of the present invention is therefore to provide a system that is suited for use in operating theatres, and which also fulfils the above-mentioned aims.

The above is provided by a lighting system of the type mentioned comprising one or more prefabricated module elements for ceilings and/or walls which elements contain one or more light sources mounted so as to be movable and adjustable, an indicator being held in the operating area or other area, means that receive optical, ultra sound or magnetic signals from said indicator, in which the light is required to be focused and which calculate the position of the indicator, and wherein said means based on the position parameters adjusts and moves light sources towards the desired absolute position or point of focus of the point device.

The light source modules are intended for operating theatres, but may also be used within other areas in which it is desirable for one or more light sources to track an event, e.g. such as an artist on a stage, dancers/ice dancers in a hall or where it is required that lighting should be directable and/or focusable on a work surfaces or events. The system may also be used at sports events where the contestants are to be tracked around a course.

As the module unit can be ceiling elements or wall elements containing one or more light sources that may be directed and focused on certain surfaces, the unit may be installed in existing operating theatres in a simple manner.

Adjustment can be carried out manually via an operating panel, or be controlled automatically through pointing at the surface or point to be lit, e.g. with a video camera (marker/visual system), a beam of light (laser), ultra sound, infrared radiation, radio frequency (transmitter/receiver) or similar, where this is connected to a processing unit that calculates and controls the light towards said point or surface.

It this connection, it should be noted that lamps are known which can direct light at a working area by using a reflecting indicator (a control electrode) in the working area, cf. DE 32 43 710.

The above publication describes a system of relative positioning, as the reflecting unit (indicator, which determines the point at which the light source should be directed) must be hit by the sensor system and then be "hooked" on in order to then pull/control the light by moving the indicator. The present invention however, aims to provide absolute positioning, so that if the pointer is brought to the desired point, the focus of the lighting unit will come together in this point.

The module unit may be connected up to several module units in order to form a controlled cluster, or some of the modules are selected to form a controlled cluster.

In the following, the invention will be described in greater detail with reference to the drawings, in which:

FIG. 1 schematically shows the principle of a possible embodiment of the present invention;

In the following, the invention is described in connection with ceiling modules, but it should be noted that the invention may also be used in connection with other forms of modules such as wall modules.

Figure 1:
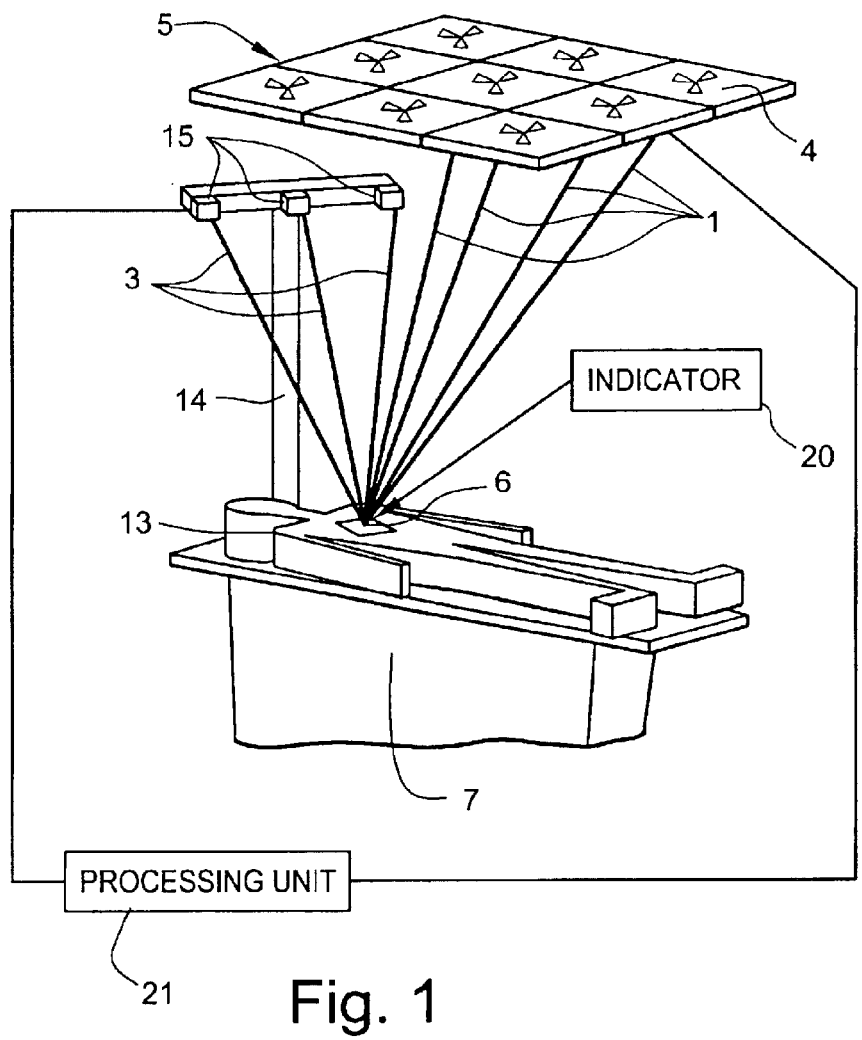

FIG. 1 schematically shows an operating table 7 with a patient 13. Reference number 6 indicates an operating area. Reference number 5 shows a cluster of lighting modules 4 mounted in the ceiling of the operating theatre. On the floor is a stand 14 with direction determining means 15 for the lighting, for instance three infrared cameras. The means 15 may be based on optical, ultra sound or magnetic tracing, for instance of the type described in DE 32 43 710. That is, the light from the modules 4 is focused automatically via an adjustment/control device by a form of indicator(s) 20 being held in the operating area or other area in which the light is required to be focused. The means 15, e.g. an infrared camera (reference number 3 indicates the signal path to/from the indicator), sees the indicator, which may for instance be two light-emitting diodes, and, by use of software that is known per se (schematically illustrated as processing unit 21) for calculation of the position of the indicator, transmits control signals to the adjusting mechanism of the light-emitting devices in the modules 4, so that the light beams 1 hit the desired area 6. The indicator may also be in the form of a radio transmitter that communicates with the adjusting mechanism for the light source.

A possible embodiment of the pointer device/indicator 20 can be formed by the surgeon having a device in the form of e.g. a helmet with e.g. infrared light-transmitting means, so that e.g. infrared cameras register the bright spot in the field, and the position of the bright spot is calculated in a manner so as to focus the light on this point.

By the position of the pointer being calculated and indicated in a Cartesian system of co-ordinates, for instance with the origin at one corner of the operating table, x along the longitudinal axis, y across and z up from the table, and by all the lighting elements having a known position in relation to this system of co-ordinates, the alpha-angle about the x-axis (in the plane of the ceiling) and the beta-angle about the y-axis (in the plane of the ceiling) may be determined based on trigonometric considerations for each light source, so as to make these hit the same specified point of focus.

A pre-defined cluster of lighting elements can be controlled manually from the control panel after the focus of the cluster has been created. In this manner, the point of focus is controlled relative to its initial position towards absolute by indicating the point of focus with the pointer device as mentioned above. In this manner, each light source can also be controlled manually. By several clusters of lighting units creating a focus at different depths (Z-position), but with the same position in the plane (XY), a highly focused light may be achieved that is more robust with respect to variations of depth in the point of focus "depth of focus").

The following describes and shows each ceiling module 4 containing one light source; naturally however, it will be possible to provide more light sources in a ceiling module, the number being dependent on the desirable or required quantity of light. The light source may be in the form of light bulbs, e.g. halogen bulbs mounted in a reflector. This is a cheap solution, but due to radiation of heat with a temperature increase in the operating area or a heat increase in the ceiling if the light source is used with heat absorbing lenses or filters, it is a rather unsuitable solution and therefore not recommended.

Use of specially constructed light-emitting diodes that have a particularly high light intensity without producing a significant quantity of heat, is a possible embodiment of the light source. These may then be installed in a fixed, close cluster (group of light-emitting diodes) in numbers that give off light corresponding to the requirement of each lighting module. This is then a self-contained lighting module that must in due course be installed in a manner so as to allow the cluster of lighting modules to be controlled in a similar manner to the above-described lighting modules.

Another solution to the light source problem is to use fibre-optic cables, where the light source generator can be placed in an area where the temperature generation does not constitute a problem. The cable will then transmit light to the fitting in the ceiling element, the end of the fibre-optic cable being attached to a ball 8 mounted in the ceiling module, which ball serves partly as an attachment/holder for the fibre cable and partly as a support/articulation whereby the light is directed at the operating area or other desired area via any filters and lenses arranged in front of the fibres. In order to increase the light output, several fibre-optic cables may be arranged side by side. In addition, it should be noted that regardless of type, the light source is preferably fixed in the x, y direction in relation to a holder (reflector), which reflector may be shaped like one half of a cup, as when using a halogen light source in a reflector, or spherical with an opening for letting the light beam out as mentioned above, by use of fibre-optic lighting cable.

When using a fibre-optic lighting cable, this may also be used for transmitting UV radiation when changing over to a UV radiation mode, for instance at night for additional sterilisation of the operating theatre. In this case, the UV radiation will not be directed at a specific area, instead the control device for the direction of the light will be wired in a manner such that the beam sweeps across the entire room.

Rather than using the same cable for this purpose, it is obviously possible to lead an extra cable to the fitting specifically for this purpose in order to avoid having to change over the light source; thus only a change-over in the operational mode of the fitting is required when the operating theatre is not in use. The fitting or the modules 4 may also be equipped with nozzles for transport of air and/or aqueous steam to the operating area. Such a device would be able to compensate for dehydration of tissue that has been exposed to the surrounding air. In general, ventilation can be effected by the modules having perforated edges, or ceiling elements in the form of ventilation modules may be positioned between the ceiling modules of light sources.

By integrating the lighting modules with air ducts, the system will be especially suited for use in operating theatres with LAF ceilings (Laminar Air Flow), so as to prevent the lighting system creating turbulence in the air flow.

Figure 2:
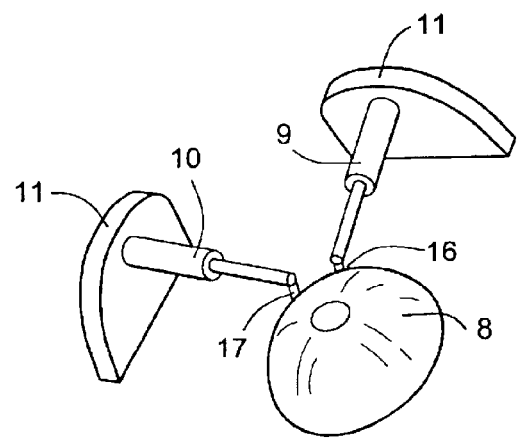
FIG. 2 shows a possible embodiment of the mechanism for controlling the direction of the light source.

The reflector with the light source or the ball with the fibre cable is arranged to be movable in the xy-plane (the plane of the ceiling), i.e. the light beam from the light source can be rotated about the y-axis and the x-axis. This is effected e.g. by means of a gyroscopic suspension system or a ball joint suspension system as indicated in FIG. 2.

The ball lies in a ball rest 12 by two identical half module plates with half a ball rest being placed up against each other, or by the ball being placed in a rest and a stop plate with a rest being mounted at the back of the ceiling module.

Figure 3:
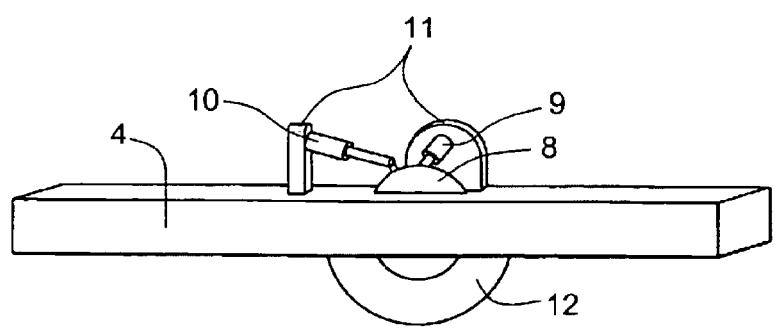
FIG. 3 is a side view of a possible embodiment of a module unit.

On the top of the suspension ball 8, which is at the back of the ceiling module 4, there is provided two attachment points 16, 17 offset by 90° with respect to each other but parallel to the plane of the ceiling when the light beam is directed downwards normal to the ceiling plane (xy plane). To the attachment points 16 and 17 are articulated respective linear actuators 9 and 10 for reciprocating movement of the reflector about the x-axis and the y-axis respectively. At their other ends, the actuators 9 and 10 are attached to lugs 11, provided on the ceiling modules 4, cf. FIG. 3. This can also be carried out by use of rotary actuators, possibly mounted in combination with a gear unit, which rotate the suspension ball/holder directly about the axis of rotation.

When using light bulbs or light-emitting diodes with a reflector, the light beam can be focused by the bulb being arranged to be movable up and down inside the reflector (e.g. paraboloidal), this movement being effected by a linear actuator that may be controlled via electronics appropriate for this purpose.

The focusing may also be effected by movable lenses.

Figure 4:
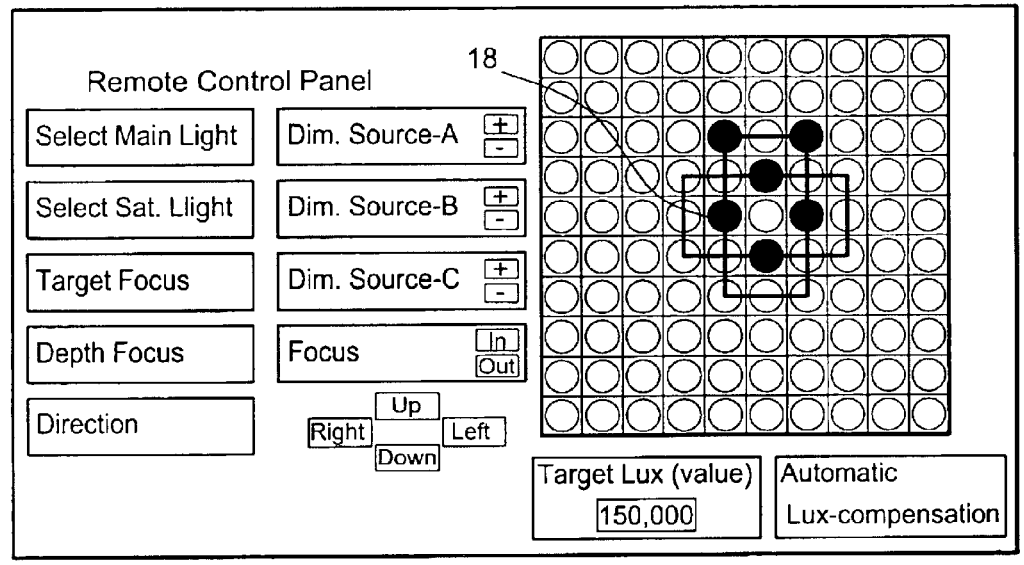
FIG. 4 shows a possible embodiment of the control panel for the lighting system.

The control panel may, as indicated in FIG. 4, consist of fields in the form of touch keys. As appears from FIG. 4, the direction of the light beam or light beams may also be controlled manually by means of the control panel, i.e. the above-described automatic setting of the lighting area can be overruled by means of the control panel.

Furthermore, the respective light sources may be selected e.g. to form a cluster that is controlled as a light source, as indicated by reference number 18 in FIG. 4.

What is claimed is:

1. A lighting system for directing or focusing light on work surfaces or events, comprising:
    at least one prefabricated module element for a ceiling and/or wall, each said module element containing at least one light source mounted so as to be movable and adjustable,
    an indicator selectively disposed in an area selectively illuminated by said at least one light source, to indicate a target toward which light from said at least one light source is to be directed, means for detecting the target indicated by the indicator and which calculate a position of the target, and means for adjusting and moving said at least one light source to direct or focus light towards the target based on the position of the target calculated by the detecting means.

2. The lighting system according to claim 1, characterised in that the indicator contains light-emitting diodes.

3. The lighting system according to claim 1, characterised in that the indicator comprises a radio transmitter.

4. The light system according to claim 1, characterised in that the module element is adapted to transport air and/or aqueous steam to an area of the target, and/or the module element is equipped with UV radiation sources that are switched on when the selectively illuminated area is not in use.

5. The lighting system according to claim 1, characterised in that the light source consists of light-emitting diodes, halogen bulbs or the end of one or more fibre-optic cables.

6. The lighting system according to claim 1, characterised in that the lighting system is further adjustable with regard to light intensity.

7. The lighting system according to claim 1, characterised in that the system comprises a processing unit that calculates and controls the light towards said target.

8. The lighting system according to claim 1, characterised in that the light source is fixed in a reflector shaped like one half of a cup or a spherical holder, and that the reflector or the holder is arranged to be moveable in a plane of the module element.

9. The lighting system according to claim 1, characterised in that a holder is attached to the module element by means of a gyroscopic suspension system or a ball joint suspension system.

10. The lighting system according to claim 1, characterised in that on the top of a suspension ball, which is at the back of the module element, there is provided two attachment points offset by 90° with respect to each other but parallel to a plane of the module element when a light beam is directed from the light source downwards normal to the plane of the module element.

11. The lighting system according to claim 1, characterised in that respective linear actuators for reciprocating movement of a holder for the light source about an x-axis and a y-axis respectively are articulated to the attachment points.

12. The lighting system according to claim 1, characterised in that the light source is mounted to be movable in the longitudinal direction of a light beam from the light source inside a reflector, where the light source is halogen bulbs or light-emitting diodes, or relative to a lens where the light source is a fibre-optic light sources for adjustment of the focus of the light beam, or the focus is changed/controlled by a reflecting, flexible reflector changing its focal point by an actuator being attached to the end of the flexible reflector and being moved in and out in the longitudinal direction of the light to stretch the reflector.

13. The lighting system according to claim 1, wherein said indicator emits at least one of optical, ultra-sound or magnetic signals and wherein said detecting means detects or receives said optical, ultrasound or magnetic signals.

14. A lighting system, preferably for use in operating theatres in which it is desirable for lighting to be directable and/or focusable on work surfaces or events, in which light sources are designed to be controlled independently in each module element or in clusters of module elements by means of a control device, characterized in that the lighting system comprises:

one or more prefabricated module elements for ceilings and/or walls, which element(s) contain(s) one or more light sources mounted so as to be movable and adjustable, an indicator being held in an operating area or other area, means that receive optical, ultra sound or magnetic signals from said indicator in which light is required to be focused and which calculate a position of the indicator, and wherein said means based on said calculated position adjust and move light sources towards an absolute position or point of focus of the indicator, wherein on a top of a suspension ball, which is at the back of the module element, there is provided two attachment points offset by 90° with respect to each other but parallel to a plane of a ceiling to which the module element is mounted when a light beam therefrom is directed downwards normal to said plane.

15. A lighting system for directing or focusing light on work surfaces or events, comprising:

at least one prefabricated module element for a ceiling and/or wall, each said module element containing at least one light source mounted so as to be movable and adjustable, an indicator to indicate a target toward which light from said at least one light source is to be directed, means for detecting the target indicated by the indicator and which calculate a position of the target, and means for adjusting and moving said at least one light source to direct or focus light towards the target based on the position of the target calculated by the detecting means, wherein the light source is mounted to be movable in a longitudinal direction of a light beam therefrom inside a reflector adjustment of the focus of the light beam.

* * * * *